US012599474B2

(12) United States Patent
Egnelöv et al.

(10) Patent No.: US 12,599,474 B2
(45) Date of Patent: *Apr. 14, 2026

(54) TUBULAR MESH SUPPORT DEVICE FOR A BREAST IMPLANT AND METHOD FOR PREPARING THE BREAST IMPLANT

(71) Applicant: NOVUS SCIENTIFIC AB, Uppsala (SE)

(72) Inventors: Per Egnelöv, Uppsala (SE); Torbjörn Mathisen, Älvsjö (SE)

(73) Assignee: NOVUS SCIENTIFIC AB, Uppsala (SE)

( * ) Notice: Subject to any disclaimer, the term of this patent is extended or adjusted under 35 U.S.C. 154(b) by 1100 days.

This patent is subject to a terminal disclaimer.

(21) Appl. No.: 17/608,828

(22) PCT Filed: May 6, 2020

(86) PCT No.: PCT/SE2020/050462
§ 371 (c)(1),
(2) Date: Nov. 4, 2021

(87) PCT Pub. No.: WO2020/226558
PCT Pub. Date: Nov. 12, 2020

(65) Prior Publication Data
US 2022/0296359 A1     Sep. 22, 2022

(30) Foreign Application Priority Data
May 9, 2019     (SE) .................................... 1950556-9

(51) Int. Cl.
*A61F 2/12*          (2006.01)
*A61F 2/00*          (2006.01)

(52) U.S. Cl.
CPC ........ *A61F 2/12* (2013.01); *A61F 2002/0068* (2013.01); *A61F 2210/0004* (2013.01);
(Continued)

(58) Field of Classification Search
CPC ....................................................... A61F 2/12
See application file for complete search history.

(56) References Cited

U.S. PATENT DOCUMENTS

| | | | |
|---|---|---|---|
| 2,978,787 A | 4/1961 | Liebig |
| 4,865,031 A | 9/1989 | O'Keeffe |

(Continued)

FOREIGN PATENT DOCUMENTS

| | | |
|---|---|---|
| CN | 1169277 A | 1/1998 |
| EP | 0 797 962 A2 | 10/1997 |

(Continued)

OTHER PUBLICATIONS

Swedish Search Report, Application No. 1950556-9, Oct. 28, 2019, 3 pages.

(Continued)

*Primary Examiner* — Marcia L Watkins
(74) *Attorney, Agent, or Firm* — Foley & Lardner LLP

(57)          ABSTRACT

The invention relates to a mesh support device (10) for supporting a breast implant (20), wherein the mesh support device (10) has a tubular shape. The invention relates further to a breast implant device for implantation in a human body, comprising a breast implant (20) and a mesh support device (10), in which the breast implant (20) is positioned, wherein the mesh support device (10) has a tubular shape. In accordance with the invention, a method for preparing a breast implant (20) for implantation in a human body is also disclosed.

9 Claims, 2 Drawing Sheets

20

10

(52) U.S. Cl.
CPC ................ *A61F 2210/0057* (2013.01); *A61F 2220/0008* (2013.01); *A61F 2230/0069* (2013.01); *A61F 2250/003* (2013.01)

(56) References Cited

U.S. PATENT DOCUMENTS

| | | | |
|---|---|---|---|
| 4,916,193 A | 4/1990 | Tang et al. | |
| 4,936,858 A * | 6/1990 | O'Keeffe ................... | A61F 2/12 623/8 |
| 4,983,184 A | 1/1991 | Steinemann | |
| 5,147,400 A | 9/1992 | Kaplan et al. | |
| 5,178,630 A | 1/1993 | Schmitt | |
| 5,496,370 A | 3/1996 | Hamas | |
| 5,686,090 A | 11/1997 | Schilder et al. | |
| 5,733,337 A | 3/1998 | Carr et al. | |
| 6,162,962 A | 12/2000 | Hinsch et al. | |
| 6,235,869 B1 | 5/2001 | Roby et al. | |
| 6,268,544 B1 | 7/2001 | Court et al. | |
| 6,319,264 B1 | 11/2001 | Tormala et al. | |
| 6,477,865 B1 | 11/2002 | Matsumoto | |
| 6,514,515 B1 | 2/2003 | Williams | |
| 6,875,233 B1 * | 4/2005 | Turner ...................... | A61F 2/12 623/8 |
| 6,988,386 B1 | 1/2006 | Okawa et al. | |
| 7,614,258 B2 | 11/2009 | Cherok et al. | |
| 7,749,273 B2 | 7/2010 | Cauthen et al. | |
| 7,875,074 B2 | 1/2011 | Chen et al. | |
| 8,016,841 B2 | 9/2011 | Magnusson et al. | |
| 8,083,755 B2 | 12/2011 | Mathisen et al. | |
| 8,313,499 B2 | 11/2012 | Magnusson et al. | |
| 8,906,047 B2 | 12/2014 | Mathisen et al. | |
| 9,566,370 B2 | 2/2017 | Mathisen et al. | |
| 9,717,825 B2 | 8/2017 | Mathisen et al. | |
| 10,342,653 B2 | 7/2019 | Mathisen et al. | |
| 10,363,127 B2 * | 7/2019 | Mlodinow ................ | A61F 2/12 |
| 2002/0010457 A1 | 1/2002 | Duchon et al. | |
| 2002/0042128 A1 | 4/2002 | Bowlin et al. | |
| 2002/0062152 A1 | 5/2002 | Dauner et al. | |
| 2002/0104335 A1 | 8/2002 | Shirasaki et al. | |
| 2003/0082148 A1 | 5/2003 | Ludwig et al. | |
| 2003/0193104 A1 | 10/2003 | Melican et al. | |
| 2004/0138762 A1 | 7/2004 | Therin et al. | |
| 2004/0172048 A1 | 9/2004 | Browning | |
| 2004/0234576 A1 | 11/2004 | Martin et al. | |
| 2005/0070930 A1 | 3/2005 | Kammerer | |
| 2005/0096499 A1 | 5/2005 | Li et al. | |
| 2005/0113849 A1 | 5/2005 | Popadiuk et al. | |
| 2005/0222591 A1 | 10/2005 | Gingras et al. | |
| 2005/0240261 A1 | 10/2005 | Rakos et al. | |
| 2005/0267325 A1 | 12/2005 | Bouchier et al. | |
| 2005/0287287 A1 | 12/2005 | Parker et al. | |
| 2005/0288797 A1 | 12/2005 | Howland | |
| 2006/0063909 A1 | 3/2006 | Gisselfalt | |
| 2006/0083767 A1 | 4/2006 | Deusch et al. | |
| 2006/0142786 A1 | 6/2006 | Mathisen et al. | |
| 2007/0142698 A1 | 6/2007 | Bourne et al. | |
| 2007/0154524 A1 | 7/2007 | Kauper et al. | |
| 2007/0299542 A1 | 12/2007 | Mathisen et al. | |
| 2008/0119848 A1 | 5/2008 | Shalaby et al. | |
| 2008/0306494 A1 | 12/2008 | Magnusson et al. | |
| 2009/0024151 A1 | 1/2009 | Shalaby et al. | |
| 2009/0024162 A1 | 1/2009 | Shalaby et al. | |
| 2009/0082864 A1 | 3/2009 | Chen et al. | |
| 2011/0112561 A1 | 5/2011 | Mathisen et al. | |
| 2012/0022646 A1 | 1/2012 | Mortarino et al. | |
| 2013/0006279 A1 | 1/2013 | Mortarino | |
| 2013/0304098 A1 | 11/2013 | Mortarino | |
| 2014/0303655 A1 | 10/2014 | Mathisen et al. | |
| 2016/0228236 A1 * | 8/2016 | Egnelöv ................... | A61F 2/12 |
| 2016/0331504 A1 | 11/2016 | Wang et al. | |
| 2018/0228598 A1 | 8/2018 | Mathisen et al. | |
| 2019/0282351 A1 | 9/2019 | Mathisen et al. | |
| 2020/0100892 A1 * | 4/2020 | Limem ................... | A61L 27/58 |
| 2020/0268945 A1 | 8/2020 | Mathisen et al. | |
| 2021/0260245 A1 * | 8/2021 | Peres ................... | A61L 27/362 |
| 2023/0146304 A1 * | 5/2023 | Egnelöv ................... | A61F 2/12 623/8 |

FOREIGN PATENT DOCUMENTS

| | | | |
|---|---|---|---|
| EP | 1 212 986 A1 | 6/2002 | |
| EP | 1 252 905 A2 | 10/2002 | |
| EP | 1 674 048 A1 | 6/2006 | |
| EP | 3 056 167 A1 | 8/2016 | |
| JP | H02-167156 A | 6/1990 | |
| JP | H04-061863 A | 2/1992 | |
| JP | 10-024054 A | 1/1998 | |
| JP | 2005-137398 A | 6/2005 | |
| WO | WO-03/092758 A1 | 11/2003 | |
| WO | WO-2004/050133 A2 | 6/2004 | |
| WO | WO-2006/116000 A2 | 11/2006 | |
| WO | WO-2007/014995 A2 | 2/2007 | |
| WO | WO-2009009684 A1 * | 1/2009 | ......... A61B 17/7097 |
| WO | WO 2014/149096 A1 | 9/2014 | |
| WO | WO 2017/066458 A1 | 4/2017 | |
| WO | WO 2020/072349 A1 | 4/2020 | |

OTHER PUBLICATIONS

International—Type Search Report, Application No. 1950556-9, Oct. 28, 2019, 5 pages.

"Standard Test Method for Bursting Strength of Textiles—Constant-Rate-of-Traverse (CRT) Ball Burst Test," ASTM—International, Designation: D 3787-01.

"Novus Scientific Announces the Sales Launch for TIGR® Maxtrix Surgical Mesh—World's 1st Long-Term Resorbable Synthetic Mesh", Press Release dated Jun. 21, 2010, http://novusscientific.com/2010/06/21.

"Novus Scientific presents initial results of the First-in-Man study for TIGR® Matrix Surgical Mesh—The world's 1st long-term resorbable synthetic mesh", Press Release dated Mar. 19, 2010, http://novusscientific.com/2010/03/19.

"Novus Scientific Receives CE Mark Approval for TIGR® Matrix Surgical Mesh—the World's First Long-Term Resorbable Synthetic Mesh.", Press Release dated Aug. 16, 2011, http://novusscientific.com/2011/08/16.

"Novus Scientific Receives FDA Clearance for TIGR® Matrix Surgical Mesh—World's 1st long-term resorbable synthetic mesh", Press Release dated Feb. 5, 2010, http://novusscientific.com/2010/02/05.

Examination Report in Australian Application No. 2008202439, Nov. 5, 2012.

Office Action in Chinese Application No. 200810178590.1, Sep. 15, 2011.

D. Roylance, "Introduction to Composite Materials," Mar. 24, 2000, pp. 1-7, Dept. of Materials Science and Engineering, MIT, Cambridge, MA.

H. Magnusson et al., US PTO Final Office Action, U.S. Appl. No. 11/808,563, dated Feb. 28, 2011.

H. Magnusson et al., US PTO Notice of Allowance, U.S. Appl. No. 11/808,563, dated Jul. 27, 2011.

H. Magnusson et al., US PTO Office Action, U.S. Appl. No. 13/617,742, dated Jan. 2, 2013.

H. Magnusson et al., USPTO Final Office Action, U.S. Appl. No. 13/617,742, dated Dec. 15, 2015.

H. Magnusson et al., USPTO Non-Final Office Action, U.S. Appl. No. 12/952,723, Feb. 13, 2012.

Henrik Magnusson et al., USPTO Notice of Allowance, U.S. Appl. No. 12/952,723, dated Jul. 25, 2012.

Office Action in Japanese Application No. 2008-153433, Nov. 13, 2012.

K. Junge et al., "Elasticity of the anterior abdominal wall and impact for reparation of incisional hernias using mesh implants," Hernia, vol. 5, No. 3, Sep. 14, 2001, pp. 113-118.

K. Van de Velde et al., "Biopolymers: overview of several properties and consequences on their applications," Sep. 11, 2001, pp. 433-442, Polymer Testing 21, Elsevier Science Ltd., Zwijnaarde, Belgium.

(56)        References Cited

OTHER PUBLICATIONS

Klinge et al., Modified Mesh for Hernia Repair that is Adapted to the Physiology of the Abdominal Wall, European Journal of Surgery, 164(12), pp. 951-960, Dec. 1998.

Mathisen et al., USPTO Office Action, U.S. Appl. No. 11/472,563, dated Oct. 28, 2009.

Partial European Search Report in European Application No. EP 0710992, Nov. 19, 2007.

T. Mathisen et al., USPTO Decision on Appeal, U.S. Appl. No. 11/019,534, dated Oct. 8, 2013.

T. Mathisen et al., USPTO Final Office Action, U.S. Appl. No. 11/472,563, dated Dec. 23, 2009.

T. Mathisen et al., USPTO Final Office Action, U.S. Appl. No. 11/019,534, dated Aug. 5, 2010.

T. Mathisen et al., USPTO Final Office Action, U.S. Appl. No. 11/019,534, dated Aug. 27, 2009.

T. Mathisen et al., USPTO Final Office Action, U.S. Appl. No. 11/472,563, dated Jun. 25, 2009.

T. Mathisen et al., USPTO Final Office Action, U.S. Appl. No. 11/808,563, dated Jan. 3, 2011.

T. Mathisen et al., USPTO Final Office Action, U.S. Appl. No. 13/004,530, dated Jan. 2, 2013.

T. Mathisen et al., USPTO Final Office Action, U.S. Appl. No. 13/312,007, dated Jan. 17, 2013.

T. Mathisen et al., USPTO Non-Final Office Action, U.S. Appl. No. 13/004,530, dated Jul. 3, 2012.

T. Mathisen et al., USPTO Non-Final Office Action, U.S. Appl. No. 13/081,998, dated Aug. 2, 2012.

T. Mathisen et al., USPTO Non-Final Office Action, U.S. Appl. No. 13/312,007, dated Mar. 30, 2012.

T. Mathisen et al., USPTO Notice of Allowance, U.S. Appl. No. 11/472,563, dated Oct. 20, 2011.

T. Mathisen et al., USPTO Office Action, U.S. Appl. No. 11/019,534, dated Feb. 11, 2008.

T. Mathisen et al., USPTO Office Action, U.S. Appl. No. 11/019,534, dated Jun. 20, 2007.

T. Mathisen et al., USPTO Office Action, U.S. Appl. No. 11/019,534, dated Aug. 28, 2008.

T. Mathisen et al., USPTO Office Action, U.S. Appl. No. 11/019,534, dated Nov. 16, 2006.

T. Mathisen et al., USPTO Office Action, U.S. Appl. No. 11/472,563, dated Nov. 12, 2008.

T. Mathisen et al., USPTO Office Action, U.S. Appl. No. 11/808,563, dated Jun. 16, 2010.

T. Mathisen et al., USPTO "Decision on Request for Rehearing", U.S. Appl. No. 11/019,534, dated Mar. 24, 2014.

T. Mathisen et al., USPTO Final Office Action U.S. Appl. No. 13/004,530, dated Aug. 15, 2014.

T. Mathisen et al., USPTO Non-Final Office Action, U.S. Appl. No. 11/019,534, dated Dec. 31, 2015.

T. Mathisen et al., USPTO Non-Final Office Action, U.S. Appl. No. 13/004,530, dated Jan. 4, 2016.

T. Mathisen et al., USPTO Non-Final Office Action, U.S. Appl. No. 13/617,742, dated Jul. 1, 2015.

T. Mathisen et al., USPTO Non-Final Office Action, U.S. Appl. No. 14/313,423, Mar. 17, 2016.

T. Mathisen et al., USPTO Notice of Allowance, U.S. Appl. No. 13/312,007, May 28, 2014.

T. Mathisen et al., USPTO Office Action, U.S. Appl. No. 13/004,530, dated May 6, 2014.

T. Mathisen et al., USPTO Office Action, U.S. Appl. No. 13/312,007, Nov. 21, 2013.

TIGR Matrix Surgical Mesh Presentation. Slideshow [online]. Novus Scientific, Oct. 7, 2011 [retrieved on Mar. 7, 2022]. Retrieved from the Internet: <URL: https://www.mynewsdesk.com/novus-scientific/documents/tigr-r-matrix-surgical-mesh-presentation-15917>. (Year: 2011).

TIGRTM Matrix Surgical Mesh, Hunting for the only long-term resorbable synthetic mesh?, Novus Scientific, Conference in Orlando, FL, Mar. 17-20, 2010.

U. Klinge et al., "Abnormal Collagen I to III Distribution in the Skin of Patients with Incisional Hernia", European Surgical Research, 2000, pp. 43-48.

USPTO Final Office Action, U.S. Appl. No. 11/019,534, Jun. 16, 2016.

USPTO Final Office Action, U.S. Appl. No. 13/004,530, May 27, 2016.

USPTO Notice of Allowance, U.S. Appl. No. 11/019,534, Dec. 21, 2016.

USPTO Notice of Allowance, U.S. Appl. No. 13/004,530, May 10, 2017.

USPTO Notice of Allowance, U.S. Appl. No. 13/312,007, Aug. 28, 2014.

USPTO Notice of Allowance, U.S. Appl. No. 14/313,423, Feb. 1, 2017.

USPTO Notice of Allowance, U.S. Appl. No. 15/635,812, Feb. 25, 2019.

USPTO Office Action, U.S. Appl. No. 13/617,742, Jun. 6, 2013.

USPTO Office Action, U.S. Appl. No. 14/313,423, Sep. 23, 2016.

USPTO Office Action, U.S. Appl. No. 15/635,812, Nov. 1, 2018.

USPTO Office Action, U.S. Appl. No. 15/669,115, Apr. 4, 2019.

USPTO Office Action, U.S. Appl. No. 15/669,115, Jul. 26, 2019.

USPTO Office Action, U.S. Appl. No. 15/669,115, Nov. 15, 2019.

USPTO Office Action, U.S. Appl. No. 16/872,489 Mar. 14, 2022.

USPTO Office Action, U.S. Appl. No. 16/427,766, Mar. 16, 2021.

W. H. de Jong et al., "Late tissue reactions and degradation of biodegradable polylactide implants. An experimental study in rats," National Institute of Public Health and the Environment (Bilthoven, The Netherlands), Report No. 605148 006, Jun. 1996, pp. 1-38.

* cited by examiner

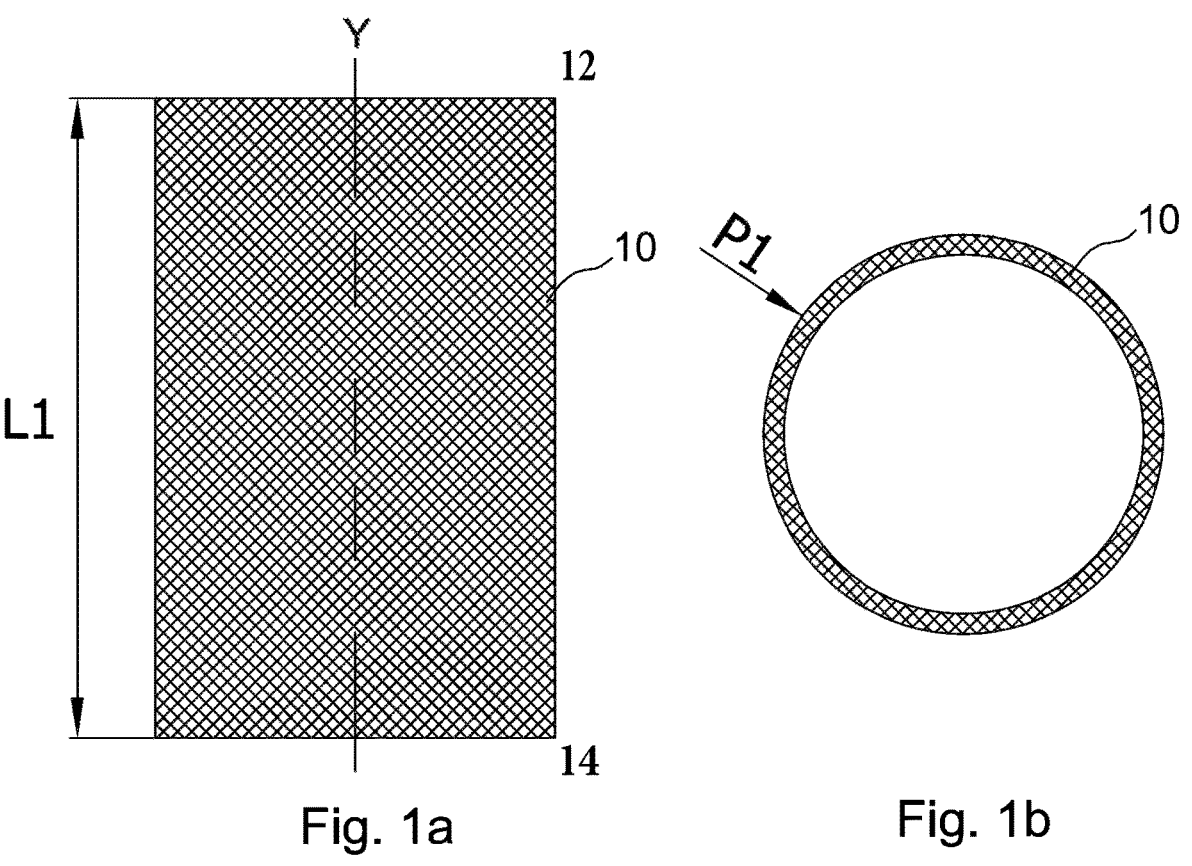
Fig. 1a                    Fig. 1b
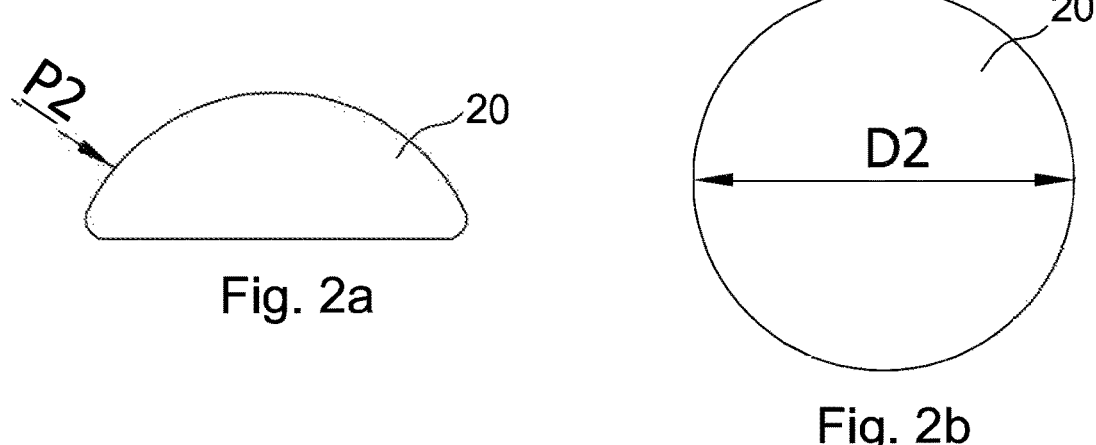
Fig. 2a                    Fig. 2b

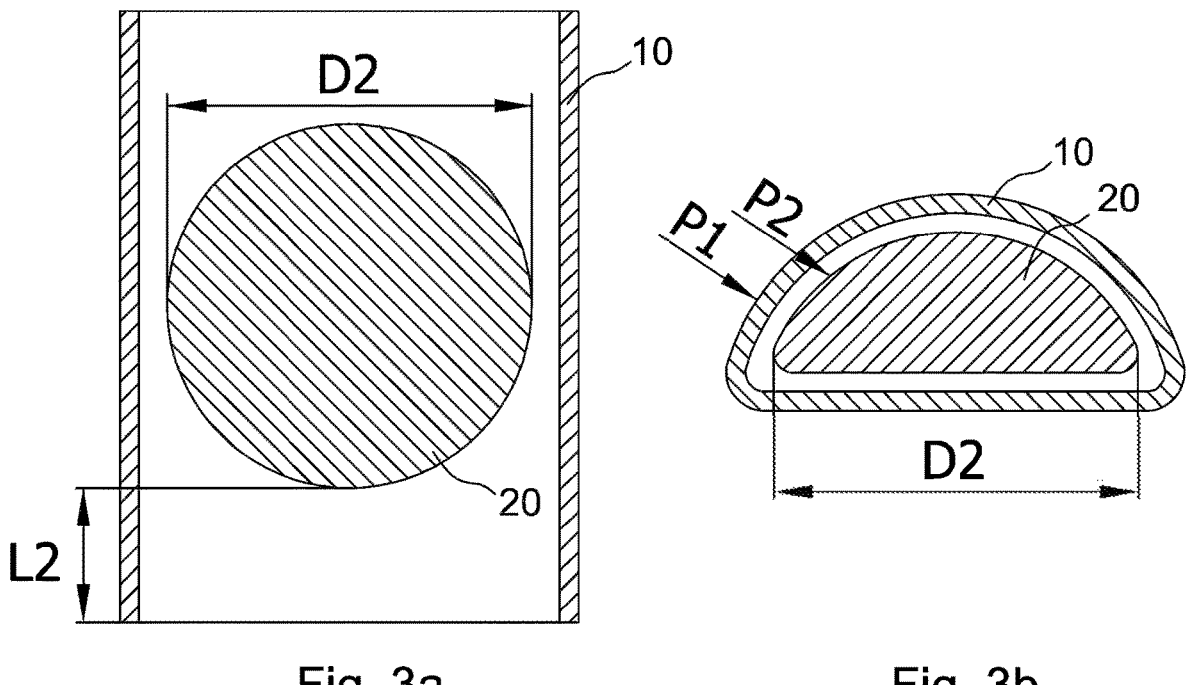
Fig. 3a
Fig. 3b
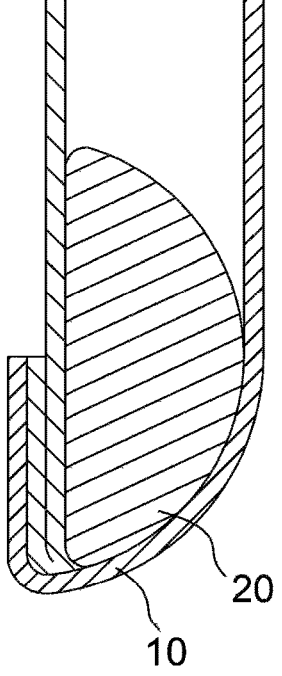
Fig. 3c

TUBULAR MESH SUPPORT DEVICE FOR A BREAST IMPLANT AND METHOD FOR PREPARING THE BREAST IMPLANT

FIELD OF THE INVENTION

The present invention relates generally to a medical support device for supporting a medical implant and relates particularly to a mesh support device for supporting a breast implant, wherein the mesh support device—before implantation of the mesh support device and the breast implant in a human body—has a tubular shape. The invention also relates to a breast implant device comprising a breast implant and a tubular mesh support device, and to a method for preparing such a breast implant device.

BACKGROUND OF THE INVENTION

A medical breast reconstruction is a procedure that typically involves the use of prosthetic breast implants, e.g. silicone or saline implants, which are placed either inside or outside the breast muscle, to recreate a female breast. Within the art of reconstructive and cosmetic breast surgery, it is further common to at least partly place the breast implant in a support device. The support device can then be attached, e.g. stitched, to the human breast tissue to thereby fixate the position of the breast implant, or the support device can simply provide a structure for facilitating and promoting tissue integration.

Support devices for breast implants come in many types and designs but are typically made from a mesh material and have a flat back wall and a concave front wall. The mesh material used can be a permanent mesh material or can be made from a biodegradable material. Examples of support devices are disclosed in the published U.S. Patent Application No. 2013/0304098 to Mortarino, which relates to a three-dimensional fabric structure in the form of a pocket in which the breast implant is to be placed. Similar support devices are further disclosed in the U.S. Pat. No. 7,875,074 to Chen et al., wherein the support devices comprise a concave receiving space, which is defined by a back wall and a front wall for at least partly receiving and supporting a breast implant therein.

A common feature of the known support devices for breast implants is that they provide a pocket in which the breast implant is to be placed. However, as stated above, breast implants come in several sizes and also shapes, which means that several support devices having pockets with corresponding sizes and shapes must be kept in store, which in itself poses a logistical problem, since a support device, which often is made from a bio-degradable material, typically has an expiry date that must not be exceeded.

Further, even if the size and shape of particular support device is well fitted to a specific breast implant, there is—due to the pocket-like shape—always a certain mismatch between the round or more or less hemispherically shaped breast implant and the outer rim area of the receiving pocket, i.e. the breast implant does not completely fill out the space where a back wall of the support device meets the front wall, which makes it difficult to exactly position the breast implant. Furthermore, many existing support devices for breast implants are by doctors and surgeons perceived to have a design that is too elaborated to be optimal from a medical perspective, i.e. the support devices require extra attention and special handling during the implantation procedure. Needless to say, any medical device which has a design that is not optimal from a medical perspective implies a certain risk for the patient.

Although a support device according to the prior art may serve its intended purpose well, it is still accompanied by problems related to its adaption to the size and shape of the breast implant that is to be supported by the support device in question. The known support devices are typically also associated with disadvantages when it comes to user-friendliness, i.e. how easy they are to handle by doctors and surgeons during an implantation procedure. A general object of the present invention is therefore to provide an improved support device for a breast implant, which support device has a design and shape that can be well and easily adapted to a span of different implant sizes and shapes. Another object of the invention is to provide an improved support device which is easy to handle during a medical implantation procedure. A further object of the invention is to provide an implant device comprising a breast implant and an improved support device, and a still further object is to envisage a method for preparing a breast implant for implantation into a human body.

SUMMARY OF THE INVENTION

The above-mentioned objects are achieved by the present invention according to the independent claims. Preferred embodiments are set forth in the dependent claims.

Embodiments of the present invention relate to a mesh support device for supporting a breast implant, wherein the mesh support device has a tubular shape. In one embodiment of the invention, the mesh support device is made by a knitting or weaving technique that prevents unraveling. In another embodiment, the mesh support device is made from a bio-degradable material; and in a still further embodiment, the mesh support device is made from at least two bio-degradable materials having different degradation times. By manufacturing a mesh support device by means of an unraveling-preventing knitting or weaving technique, a more reliable mesh support device is provided, which can be fixedly anchored, e.g. sutured, stitched or stapled, to human breast tissue; and by making the mesh support device from a bio-degradable material, long-term complications, which may be associated with permanent mesh materials, can be avoided. According to one embodiment, a mesh support device can be made from two different bio-degradable materials having different degradation times, something which can promote tissue integration as the mesh support device gradually degrades over time.

A mesh support device according to the present invention is a soft and pliable object, which furthermore can possess some elasticity. Throughout this application, the term "tubular", when used to describe the shape of a mesh support device according to the invention, is therefore defined as the basic or nominal shape of the mesh support device, i.e. the mesh support device can (i.e. is able to) assume a tubular shape; for example when being threaded over a cylindrical object having the same diameter as the mesh support device, but it is not necessary that the mesh support device actually has a tubular shape throughout its life time, or even at any time during its lifetime.

The present invention is further related to a breast implant device for implantation in a human body, which breast implant device comprises a breast implant and a mesh support device, in which the breast implant is positioned, wherein the mesh support device has a tubular shape. The breast implant can at least partly be made from silicone or saline, or a combination thereof. In one embodiment of the breast implant device, the breast implant has a rounded frontside and an essentially flat backside and that the mesh support device covers both the frontside and the backside and has been folded backwards to lie essentially parallel with the backside of the breast implant. By this configuration, the breast implant is always provided with a fixed and firm support from one side, which side, when implanted, constitutes the underside of the breast implant device. When the simplest design of a breast implant is resting on a table it can best be described as one half of an ellipse or a semi-elliptic design, which can be used to deduce the circumference or perimeter of the implant by the use of the well-known approximation of Ramanujan (see, e.g., Villarino, M B; "A note on the accuracy of Ramanujan's approximative formula for the perimeter of an ellipse"; vol 7(1), article 21, 2006, p. 1, formula 1.1). Breast implants from major manufacturer are characterized by a diameter, D2, and a projection, H, which can be exchanged by the major and minor axis respectively of a half ellipse. The circumference or perimeter, P2, of the breast implant can now be approximated with the use of Ramanujan's approximation. In another embodiment, the breast implant has a largest circumference or perimeter P2 and the mesh support device has a circumference or perimeter P1, wherein P1≥P2; and in a preferred embodiment, the perimeter of the mesh support device has a perimeter P1 such that P1≥P2+X mm, where X is in the interval of 5 mm to 60 mm, and more preferably in the interval of 20 mm to 45 mm. By choosing a mesh support device having a larger perimeter than the breast implant positioned therein, a doctor or surgeon is advantageously provided with extra mesh material at the lateral sides of the breast implant device to securely fixate, e.g. by stitching, suturing or stapling, the breast implant device in the human breast tissue. With, for example, X=20 mm there is 5 mm extra mesh material on each lateral side of the breast implant to be utilized for fixate the breast implant. In embodiments of a breast implant device, the mesh support device can be made from one bio-degradable material, or from several bio-degradable materials, which can have different degradation times. As will be thoroughly explained below, for the mesh support device to firmly support a breast implant, a length L1 of the mesh support device should be longer than the diameter D2 of the breast implant, and preferably L1≥D2+100 mm.

The present invention is also related to a method for preparing a breast implant for implantation in a human body, which method comprises the steps: providing a breast implant having a rounded frontside and an essentially flat backside; determining the largest diameter D2 of the breast implant; providing a mesh support device having a tubular shape with a length L1 and a diameter D1 with a corresponding perimeter P1, where P1≥P2, and preferably P1≥P2+X mm, where X is in the interval of 5 mm to 60 mm, and more preferably 20 mm to 45 mm, and L1≥D2+100 mm; positioning the breast implant in the mesh support device such that a rim of the breast implant is directed in the longitudinal direction of the mesh support device and such that a first portion of the mesh support device extends a distance L2 beyond the rim of the breast implant; and folding the first portion backwards to lie parallel with the essentially flat backside of the breast implant. In one embodiment of the method L2 is more than 50 mm and P1≥P2+20 mm. By this method for preparing a breast implant, the breast implant will be fully supported by the mesh support device from one side, which side, when implanted, will constitute the underside of the breast implant device. The preparation method according to the invention can be performed in connection with a medical implant procedure, or can be done in long advance such that the breast implant and the mesh support device are sterilized and packaged together.

BRIEF DESCRIPTION OF THE DRAWINGS

FIG. 1a illustrates schematically a side-view of a tubular mesh support device according to the present invention;

FIG. 1b illustrates schematically a cross-sectional top-view of the tubular mesh support device in FIG. 1a;

FIG. 2a illustrates schematically a side-view of a breast implant;

FIG. 2b illustrates schematically a top-view of the breast implant in FIG. 2a;

FIG. 3a illustrates schematically an intermediate configuration for a breast implant device comprising the breast implant of FIGS. 2a-b and the tubular mesh support device of FIGS. 1a-b.

FIG. 3b illustrates schematically a top-view of the intermediate configuration shown in FIG. 3a; and FIG. 3c illustrates schematically a final configuration for the breast implant device comprising the breast implant of FIGS. 2a-b and the mesh support device of FIGS. 1a-b.

DETAILED DESCRIPTION OF PREFERRED EMBODIMENTS

A mesh support device 10 according to the present invention is schematically depicted in FIG. 1a and FIG. 1b, where FIG. 1a shows the mesh support device 10 in a side-view and FIG. 1b shows the support device 10 in a cross-sectional view seen from above (or from below). The mesh support device 10 is an elongated object that is tubular and is configured to receive a breast implant. For clarity of illustration only, the mesh support device 10 has in FIG. 1b been given a considerably enlarged wall-thickness. As can be seen from FIG. 1a, the mesh support device 10 is an elongated object with a length L1 that extends in a longitudinal direction indicated by the longitudinal axis Y; and FIG. 1b shows that the mesh support device has a circular cross-section with a diameter D1 and a corresponding perimeter P1, i.e. the mesh support device is a tubular object, where the meaning of the term "tubular" has been defined above. The mesh support device 10 has a first end 12 and a second end 14 where at least the first end has an opening configured to receive a breast implant. The second end may have an opening but it is preferably closed or sealed. In one embodiment the diameter D1 of the mesh support device is essentially the same along the longitudinal axis Y from the first end to the second end. In one embodiment the length L1 of the mesh support device 10 is preferably the diameter of the breast implant (D2) to be placed in the support device plus 100-300 mm (i.e. D2+100-300 mm).

The mesh support device 10 can be made by means of any known knitting or weaving technique, and it is preferred that the mesh for the support device is made by a technique that prevents unraveling of the mesh support device 10. One example of such a knitting technique is warp-knitting, which is a family of knitting methods in which the yarn zigzags along the length of the fabric, i.e. following adjacent columns of knitting rather than a single row. By using a manufacturing method that prevents, or at least reduces the risk of, unraveling, the mesh support device can be more reliable anchored (e.g. stitched, sewed, sutured or stapled) to the human breast tissue during and after implantation of a breast implant. Unraveling is preferred since the length of the support device 10 may then be easily adjusted by cutting.

In one embodiment the mesh support device 10 is a knitted material that is stretchable or expandable to allow expansion of the diameter D1 of the mesh support device. In that way the diameter D1 may be slightly smaller than the diameter of the breast implant so that when the implant is placed in the support device 10 thereby expanding the diameter of the support device the support device will provide a tight and supporting encapsulation of said implant.

In a preferred embodiment, the mesh of the mesh support device 10 is made from a degradable material, and preferably from a bio-degradable material, which means that the material in question can be resorbed by the human body. By using a degradable material, which degrades inside the body, complications that are known to sometimes be associated with permanent mesh products can be avoided. Examples of materials in the fibers or yarns that constitute the mesh of the mesh support device 10 are (a) resorbable polymers with a relatively short degradation time, and non-limiting examples are polymers or copolymers made from the monomer glycolide in pure form, or in combination with paradioxanone, lactide, trimethylene carbonate or caprolactone, or polymers or copolymers made from the monomer paradioxanone in its pure form, or in combination with lactide, trimethylene carbonate or caprolactone; or (b) resorbable polymers with a relative long degradation time, and non-limiting examples are polylactide and polyurethanes, e.g. polyureaurethanes, polyesterurethanes and polycarbonateurethanes; or (c) any combinations thereof.

As indicated above, several materials can be combined in a single mesh support device according to the present invention, and a suitable mesh is commercially available under the tradename TIGR® Matrix Surgical Mesh and is sold by the company Novus Scientific. This mesh, which is described in U.S. Pat. Nos. 9,566,370, 8,083,755 and 8,016, 841, comprises two different polymers having different degradation times, and it is believed that the resulting gradual degradation can promote tissue integration of a mesh support device made by this particular mesh. However, although synthetic and degradable materials are believed to be advantageous, a mesh support device according to the present invention can be made from permanent (non-degradable, non-resorbable) synthetic materials or even from biological materials, and any combination thereof.

The mesh support device 10 is intended to be used together with a breast implant, and in FIG. 2*a* and FIG. 2*b*, an example of such a breast implant 20 is schematically illustrated, where the breast implant 20 is shown in a cross-sectional side-view in FIG. 2*a* and in a top-view in FIG. 2*b*. The breast implant 20, which, for example, can be made from silicone or saline, or a combination thereof, has a generally hemispherical shape with a rounded and convex upper part, also referred to as frontside, which, when implanted, is protruding forward from the human breast area, and an essentially flat lower part, also referred to as the backside, which, when implanted, rests against tissue, e.g. the breast muscle, located in the human breast area. The breast implant 20 has a diameter, i.e. a largest diameter, D2 and a corresponding perimeter P2 as is seen and defined in FIG. 2*b*.

FIG. 3*a* illustrates in one view how the breast implant 20 is positioned inside the mesh support device 10, and it can be seen that the breast implant 20 is placed such that a rim of the breast implant 20 is directed along the longitudinal axis Y of the mesh support device 10 and that the upper side or frontside of the breast implant 20 points in a direction that is transverse to the longitudinal axis Y. The position of the breast implant 20 within the mesh support device 10 is also illustrated from a top-view in FIG. 3*b*. From especially FIG. 3*b* it can further be seen that the perimeter P1 of the mesh support device 10 can be chosen such that the perimeter P1 is larger than the perimeter P2 of the breast implant 20. By selecting a mesh support device having a larger perimeter than the perimeter of a breast implant positioned in the mesh support device, a doctor or surgeon is provided with extra mesh material at the lateral sides outside of the breast implant. This extra mesh material can then be used for fixation (e.g. by stitching, suturing or stapling) of the mesh support device in human breast tissue.

From FIG. 3*a* it can further be seen that the breast implant 20 is placed in the mesh support device 10 such that the tubular mesh support device 10 in the longitudinal direction Y extends on both sides of the breast implant 20, and it can in particular be seen that the mesh support device 10 extends a first portion having length L2 beyond the rim of the breast implant 10. This first portion with length L2 will, when the mesh support device 10 and the breast implant 20 have been implanted in a human being, constitute a lower part, and the first portion is therefore also referred to as a lower portion of the mesh support device 10. In a preferred embodiment of the invention, the breast implant 20 is positioned such that the length L2 is more than 50 mm. The advantage of placing the breast implant 20 such that the mesh support device 10 extends a distance L2 beyond the rim (i.e. the lower rim) of the breast implant 20 will be apparent from the description below in conjunction with FIG. 3*c*.

FIG. 3*c* illustrates from another view the position of the breast implant 20 within the mesh support device 10. Here, the usefulness of arranging the breast implant 20 such that a first or lower portion of the mesh support device 10 extends a distance L2 outside the rim of the mesh support device 10. By this arrangement, the first or lower portion of the mesh support device can be folded backwards to lie essentially flat and parallel with the backside of the breast implant 20; and it can further be seen that by folding the lower portion of the mesh support device 10 backwards, the breast implant 20 is firmly supported by the lower portion of the mesh support device. Thus, by providing a mesh support device, which, in accordance with the present invention, has a tubular shape, and a breast implant, which is correctly positioned within the mesh support device (i.e. such that a first or lower portion of the mesh support device extends beyond a (lower) rim of the breast implant), a lower part of the breast implant fits snuggly in a lower portion of the mesh support device although the relative sizes and shapes of the breast implant and the mesh support device, respectively, are not perfectly adapted to each other. This contrasts with support devices having a pocket-shaped receiving space, where there is typically an empty area, i.e. a mismatch, between a breast implant and the support device at the area where a backside of the support device meets a frontside thereof.

Before a medical breast implantation procedure commences, a breast implant is prepared for the procedure. During this preparation, a breast implant is suitably positioned within a mesh support device, to create a breast implant device comprising the mesh support device and the breast implant. When using a mesh support device according to the present invention such a preparation procedure comprises the steps of: (a) providing a breast implant having a rounded or elliptic-like frontside and an essentially flat backside; (b) determining the diameter D2 of the breast implant; (c) providing a mesh support device having a tubular shape with a length L1 and a diameter D1, where the corresponding perimeters P1≥P2 and L1≥D2+100-300 mm; (d) positioning the breast implant in the mesh support device such that a rim of the breast implant is directed in the longitudinal direction of the mesh support device and such that a first portion of the mesh support device extends a distance L2 beyond the rim of the breast implant; and (e) folding the first portion backwards to lie parallel with the essentially flat backside of the breast implant. In a preferred embodiment of the method, L2 can be between 30 mm to 120 mm, and more preferably 50 mm to 100 mm, and P1≥P2+X, where X is in the interval of 5 mm to 60 mm, and more preferably from 20 mm to 45 mm.

Although the present invention has been described with reference to specific embodiments, also shown in the appended drawings, it will be apparent to those skilled in the art that many variations and modifications can be done within the scope of the invention as described in the specification and defined with reference to the claims below.

The invention claimed is:

1. A breast implant device for implantation in a human body, comprising:
- a breast implant (20); and
- a mesh support device (10), in which the breast implant (20) is positioned,
- wherein the mesh support device (10) is elongated so as to extend from a first end to a second end,
- wherein the mesh support device (10) has an opening at the first end through which the breast implant (20) has been inserted, and
- wherein the breast implant (20) has a rounded frontside and an essentially flat backside and the mesh support device (10) comprises:
  - a front portion that covers the frontside of the breast implant,
  - a back portion that covers the backside of the breast implant, and
  - a folded portion that is folded backwards along the back portion so as to lie essentially parallel with the backside of the breast implant (20) and contact a back surface of the back portion.

2. The breast implant device according to claim 1, wherein the breast implant (20) at least partly is made from silicone and/or saline.

3. The breast implant device according to claim 1, wherein the breast implant has a diameter D2 and a perimeter P2 and the mesh support device has length L1 and a perimeter P1, wherein P1≥P2 and L1≥D2+100 mm.

4. The breast implant device according to claim 3, wherein P1≥P2+X mm, where X is in an interval of 5 mm to 60 mm.

5. The breast implant device according to claim 3, wherein P1≥P2+X mm, where X is in an interval of 20 mm to 45 mm.

6. The breast implant device according to claim 1, wherein the mesh support device (10) is made from a bio-degradable material.

7. A method for preparing a breast implant (20) for implantation in a human body, comprising the steps of:
- providing a breast implant (20) having a rounded frontside and an essentially flat backside;
- determining the diameter D2 of the breast implant (20);
- providing a mesh support device (10) having a tubular shape with a length L1 and a diameter D1, wherein L1≥D2+100 mm, and wherein a perimeter P1 of the mesh support device (10) is greater than or equal to a perimeter P2 of the breast implant (20);
- positioning the breast implant (20) in the mesh support device (10) such that such that a portion of the mesh support device (10) extends a distance L2 beyond a rim of the breast implant (10); and
- folding said portion backwards such that:
  - a front portion of the mesh support device (10) covers the frontside of the breast implant,
  - a back portion of the mesh support device (10) covers the backside of the breast implant, and
  - the folded portion is folded backwards along the back portion so as to lie essentially parallel with the backside of the breast implant (20) and contact a back surface of the back portion.

8. Method according to claim 7, wherein L2 is more than 50 mm and P1≥P2+X mm, where X is in an interval 5 mm to 60 mm.

9. Method according to claim 7, wherein L2 is more than 50 mm and P1≥P2+X mm, where X is in an interval of 20 mm to 45 mm.

* * * * *